United States Patent [19]

Gessell

[11] Patent Number: 4,511,669

[45] Date of Patent: Apr. 16, 1985

[54] HIGH EFFICIENCY CATALYSTS FOR VARYING OLEFIN POLYMER MOLECULAR WEIGHT DISTRIBUTION

[75] Inventor: Donald E. Gessell, Ponca City, Okla.

[73] Assignee: E. I. Du Pont de Nemours and Company, Wilmington, Del.

[21] Appl. No.: 523,867

[22] Filed: Aug. 18, 1983

Related U.S. Application Data

[63] Continuation-in-part of Ser. No. 429,631, Sep. 30, 1982, abandoned.

[51] Int. Cl.$^3$ ............................ C08F 4/02; C08F 4/64; C08F 4/68; C08F 4/62

[52] U.S. Cl. .................................. 502/110; 502/104; 502/116; 502/117; 502/119; 502/128; 502/133; 502/134; 502/152; 526/124

[58] Field of Search ............... 502/104, 110, 116, 119, 502/128, 133, 134, 125, 117

[56] References Cited

U.S. PATENT DOCUMENTS

| | | | |
|---|---|---|---|
| 3,135,809 | 6/1964 | Bosmajian | 502/114 X |
| 4,218,339 | 8/1980 | Zucchini et al. | 502/111 |
| 4,258,167 | 3/1981 | Tsubaki et al. | 502/115 |
| 4,335,016 | 6/1982 | Dombro | 502/107 |
| 4,357,448 | 11/1982 | Tsubaki et al. | 502/154 X |
| 4,374,755 | 2/1983 | Berge et al. | 502/167 |
| 4,440,869 | 4/1984 | Shannon et al. | 502/104 |
| 4,458,027 | 7/1984 | Berge et al. | 502/104 |

*Primary Examiner*—Patrick Garvin
*Attorney, Agent, or Firm*—Cortlan R. Schupbach

[57] ABSTRACT

Catalysts having high efficiency in preparing olefin polymers while controlling molecular weight distribution are disclosed. The catalysts utilize magnesium siloxide supports and the product polymer molecular weight distribution can be controlled by the catalyst preparation.

30 Claims, No Drawings

HIGH EFFICIENCY CATALYSTS FOR VARYING OLEFIN POLYMER MOLECULAR WEIGHT DISTRIBUTION

This is a continuation-in-part of application Ser. No. 429,631 filed Sept. 30, 1982 and now abandoned.

This invention relates to catalysts having high efficiency in preparing olefin polymers while controlling molecular weight distribution. More specifically, this invention relates to such catalysts and a method of preparing them utilizing magnesium polysiloxide or magnesium siloxide supports wherein molecular weight distribution is altered by the addition of alkyl aluminum chloride compounds.

Many catalysts are known which utilize organo-magnesium complexes in order to manufacture polyolefin polymers. However, in general, these catalysts have fairly low catalyst efficiencies in order to produce polymers with high bulk densities. When catalyst efficiencies have been increased, generally polymers of lower bulk density have been produced. These catalysts generally require complex preparation techniques. In addition, these catalysts do not provide the flexibility of varying polymer molecular weight distributions to fit particular applications.

It is known in the art that polyolefin polymers such as polyethylene and copolymers of polyethylene and other monomers are useful for a large variety of applications. Methods of fabricating articles from these polymers include film blowing, injection molding, blow molding and the like. However, the molecular weight distribution of the polymer is critical in determining whether the polymers are suitable for these various applications. For example, in injection molding using polyolefin polymers, a narrower molecular weight distribution is preferred for optimum products as compared to blow molding techniques, wherein a broader molecular weight distribution is preferred.

Magnesium-containing catalysts known in the prior art include those described in U.S. Pat. No. 4,027,089 which prepares polymerization catalysts by reacting an organo-aluminum-magnesium complex containing siloxide groups with a titanium compound having at least one halogen atom. In Table 5 of this reference, where a siloxane was used as a catalyst component, catalyst efficiencies of about 500,000 grams of polyethylene per gram of titanium were reported. The examples show catalysts prepared at Cl/Mg atomic ratios of 5–10 yielded a narrow molecular weight distribution polyethylene.

U.S. Pat. No. 3,907,759 prepares a catalyst by reacting a magnesium siloxide with a titanium compound, requiring the titanium compound to contain a halogen. U.S. Pat. No. 4,218,339 describes polymerization catalysts prepared by reacting the reaction product of an alkyl magnesium chloride and polymethylhydridosiloxane with tetra-n-butyltitanate and silicon tetrachloride. Highest catalytic activity in this reference is shown in Example 20. The reference describes various halogenating agents which are useful, but does not include the use of aluminum compounds containing chloride.

U.S. Pat. Nos. 4,039,472, 4,105,846, 4,199,476, and 4,120,699 all describe catalysts prepared from magnesium alkoxides, titanium alkoxides and ethyl aluminum dichloride. Belgium Pat. No. 819,609 describes similar catalysts, except the magnesium alkoxide is prepared insitu from magnesium metal and an alcohol, and reports catalyst efficiency (as set forth in Example 16) as 540,000 grams of polyethylene per gram of titanium. European patent application No. 38565 describes catalysts similar to those of U.S. Pat. No. 4,218,339, except that electron donor compounds are included in the catalyst preparation.

U.S. Pat. No. 4,115,319 reacts halogenated magnesium compounds with titanium compounds to obtain a reaction product then employs a silicon compound after or during halogenation of the magnesium compound. Column 4, lines 23 to 30 describe the transition metal/Mg atomic ratio ranges between 0.02 and 20 and the halogen/transition metal ratio as between 0.5 and 100. Resultant Cl/Mg atomic ratios are betweeen 0.01 and 2000. Ethylene homopolymers prepared using these catalysts are described as having a narrow molecular weight distribution.

U.S. Pat. Nos. 4,330,646; 4,330,647; 4,330,651 and 4,335,229 describe polymerization catalysts having mole ratios of alkoxy plus siloxy to magnesium plus aluminum of less than 2.0. U.S. Pat. No. 4,374,755 teaches the use of magnesium disiloxide compounds and methods for preparing them. The application also discloses these compounds to be useful starting materials for the preparation of active catalysts for olefin polymerization. However, this reference does not disclose catalysts of high efficiency or catalysts capable of varying molecular weight distribution.

It would therefore be of great benefit to the art to provide a method of preparing catalysts having high efficiency and capable of altering molecular weight distribution.

It is therefore an object of the invention to provide a catalyst having high efficiency for the polymerization of olefins and a method of preparing such catalysts. Other objects will become apparent to those skilled in this art as the description proceeds.

I have now discovered that high efficiency catalysts having the capability of varying the molecular weight distribution of the polymer or copolymer obtained can be prepared from a magnesium containing support of the general formula

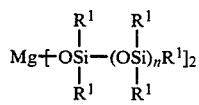

wherein each $R_1$ is, independently, hydrogen, halogen, alkyl groups, cycloalkyl groups, alkaryl groups, aralkyl groups, aryl groups, or alkoxy groups containing from 1 to 20 carbon atoms, each of which can be further substituted with halogen, and n is greater than 0, usually 0.05 or higher. When utilizing these supports, n refers to an average of these units in the total support such that while the value of n can vary from molecule to molecule, the average value will be greater than 0. Preferably n is from about 0.05 to about 50. These polymeric support materials are contacted with a non-halide transition metal alkoxide, and finally halogenated to produce the polymerization catalyst.

More concisely, the catalyst of the present invention can be prepared by a method comprising (1) reacting a hydropolysiloxane of the general formula $$[R_a{}^1H_bSiO_{\frac{4-(a+b)}{2}}]_m$$

with a dialkyl magnesium or alkyl magnesium alkoxide of the general formula RMgR or RMgOR to produce a reaction product having an SiO/Mg molar ratio of at least 1.0 and contacting the reaction product with (2) at least one non-halide transition metal alkoxide having at least one of the general formulas $$RO[M(OR)_2O]_pR$$

or $$[MO_q(OR)_r$$

or $$R_xM(OR)_y$$

then; (3) reacting the mixture of (1) and (2) with a halogenating agent to obtain a polymerization catalyst having a halogen to magnesium ratio of at least 2.0, wherein each R is, independently, hydrogen, an alkyl group containing from 1 to 20 carbon atoms, an aryl group, aralkyl group or alkaryl group which containing from 6 to 20 carbon atoms, (a) and (b) are greater than 0, where the sum of (a) and (b) does not exceed 3; m is one or more; q is from 0 to 1, and r is 2 to 4, wherein $2_{q+r}$ is equal to the valence of M; x+y is equal to the valence of M, and p is greater than one. M is generally any transition metal capable of forming a polymerization catalyst, but is preferably titanium, vanadium chromium, zirconium, or mixtures of these.

In place of hydropolysiloxanes, silyl ester of the general formula

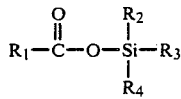

I and/or poly[oxy(silylene) esters] of the general formula

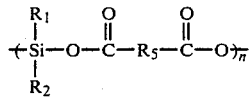

II can be used, wherein $R_1$, $R_2$, $R_3$ and $R_4$, are, independently, hydrogen, halide, alkyl and alkoxy groups containing from 1 to 30 carbon atoms, aryl aryloxy, cycloalkyl and cycloalkoxy groups containing from 6 to 30 carbon atoms, $R_5$ is an alkyl group containing from 1 to 30 carbon atoms, a cycloalkyl group, alkaryl group, aralkyl group, aryl group or bicycloalkyl group containing from 6 to 30 carbon atoms and n is greater than 2.

The reaction product of a silicon compound and dialkyl magnesium and/or alkyl magnesium alkoxide can be combined with the halogenating agent and transition metal alkoxide in any order. However, it is preferred, for slurry polymerizations, to combine the reaction product first with the transition metal alkoxide, followed by the halogenating agent. For solution polymerizations either halogenating agent followed by transition metal alkoxide or the slurry preferred order of addition is preferred.

The silicon to magnesium molar ratio is such that substantially all of the magnesium alkyl is converted to magnesium siloxides. This silicon to magnesium mole ratio must be at least 2:1 when starting with a dialkylmagnesium, but can be much higher. The silicon to magnesium mole ratio must be at least 1:1 when starting with an alkylmagnesium alkoxide, but can be much higher.

In solution polymerization systems, magnesium to titanium mole ratios should range from about 4:1 to about 200:1 respectively, but the most preferred range is from about 10:1 to about 100:1. As the molar ratio of magnesium to titanium increases, catalyst efficiency increases, however along with this catalyst efficiency increase is found an increase in catalyst residues associated with magnesium. Most notable of such residues are chloride ions. Therefore those skilled in the art will realize that the magnesium to titanium ratio must be selected to compromise between chlorine and titanium levels in the polyethylene obtained, since chlorine levels which are too high provide a corrosive polyethylene, and in contrast low titanium levels are required for color-free or white polyethylene.

A preferred hydropolysiloxane utilized in the preparation of the catalyst of this invention has an (a) value of from 0.1 to 2, and a (b) value of 1, 2, or 3, wherein the sum of (a) and (b) does not exceed 3. Representative but non-exhaustive examples of hydropolysiloxanes useful in the practice of the instant invention are polymethylhydrosiloxane (PMHS), polyethylhydrosiloxane, polyethoxyhydrosiloxane, polymethylhydro-dimethylsiloxane copolymer, polymethylhydro-methyloctylsiloxane copolymer, polyethoxyhydrosiloxane, tetramethyldisiloxane, diphenyldisiloxane, trimethylcyclotrisiloxane, tetramethylcyclotetrasiloxane, polyphenylhydrosiloxane, polyeicosylhydrosiloxane, polychlorophenylhydrosiloxane, and mixtures of these.

Representative but non-exhaustive examples of dialkyl magnesium compounds useful in preparing the catalyst of the present invention are dibutylmagnesium, n-butyl-secbutylmagnesium, butylethylmagnesium, butyloctylmagnesium, dieicosylmagnesium, di-n-hexylmagnesium.0.02 trimethylaluminum, di-n-butylmagnesium.2 triethylaluminum, di-n-butylmagnesium.0.1 triethylaluminum, dibutylmagnesium .½ triisobutylaluminum, dibutylmagnesium, : 2 triisobutylaluminum, butyloctylmagnesium.2 triisobutylaluminum, butyloctylmagnesium.½ triethylaluminum, butylethylmagnesium. 0.1 triethylaluminum, and mixtures of these.

Representative but non-exhaustive examples of alkylmagnesium alkoxides are butylmagnesium butoxide and butylmagnesium propoxide. These materials can be added separately or prepared in-situ, such as by the reaction of one mole of alcohol with one mole of dialkylmagnesium.

Representative but non-exhaustive examples of the transition metal alkoxides useful in the preparation of the present invention are tetraisopropyltitanate, tetra-n-butyltitanate, tetrabis(2-ethylhexyl)titanate, tri-n-butyl vanadate, tetra-n-propylzirconate and tetra-n-butylzirconate, isopropyltitanate decamer, i.e. iso-$C_3H_7$-O[Ti(O-iso-$C_3H_7)_2$-O]$_{10}$ iso$C_3H_7$, butyl (triisopropoxy)titanium, tetraeicosyltitanate, and mixtures thereof.

Halogenating agents useful in the practice of the present invention do not generally include transition metal halides, since the use of such halogenating agents places additional reduced or unreduced transition metal halide in the catalyst. However, such halogenating agents can be used if desired to alter the efficiency of the catalyst. Halogenating can be either liquid or gaseous materials capable of solution with a hydrocarbon to be useful. Representative but non-exhaustive examples of halogenating agents useful in the present invention are methylaluminum dichloride, methylaluminum sesquichloride, isobutylaluminum dichloride, isobutylaluminum sesquichloride, ethylaluminum dichloride, diethylaluminum chloride, ethylaluminum sesquichloride, $SnCl_4$, $SiCl_4$, HCl, $HSiCl_3$, aluminum chloride, ethylboron dichloride, boron chloride, diethylboron chloride, $HCCl_3$, $PCl_3$, $POCl_3$, acetyl chlorides, thionyl chloride, sulfur chloride, methyl trichlorosilane, dimethyl dichlorosilane, $TiCl_4$, $CCl_4$, tertiary butyl chloride, α-chloro-toluene and $VCl_4$. Of these, alkylaluminum sesquichloride, dialkyl aluminum chlorides and alkylaluminum dichlorides where the alkyl group is methyl, ethyl or isobutyl are preferred.

I have found that altering the halogen to magnesium ratio alters the molecular weight distribution, independent of support solubility, in slurry polymerizations. For example, changing the chlorine to magnesium ratio from 4 to 1 to 8 to 1 respectively will broaden the molecular weight distribution of the polymer. It is preferred that the ratio of halogen, preferably chlorine, to magnesium range from about 3 to 1 to about 16 to 1 respectively.

Transition metal halide halogenating agents are not as preferred as non-transition metal halides for the purpose of the present invention. It appears that the transition metal halides provide an excess of transition metal to the reaction, which transition metal is not fully reduced and thus decreases catalytic activity. However, these materials are operable in the present invention. Most preferred halogenating agents are chlorinating agents and of these diethylaluminum chloride, ethylaluminum dichloride ethylaluminum sesquichloride and methyl and isobutyl analogues of these are preferred.

In order to broaden molecular weight distribution of produced polymers, it is necessary that the Cl/Mg atomic ratio produced by transition metal halides be less than about 0.5, the additional chloride in the final catalyst obtained from an aluminum or boron compound, or mixtures of these, which chloride is added in a final chlorinating step. Thus, as described in this specification, at least 80 mole percent of the total chloride in the final Cl/Mg ratio is obtained from aluminum or boron sources, or mixtures of these. It is preferred that even more of the total chloride be obtained from aluminum of boron 90 mole percent).

The molecular weight distribution in slurry polymerization systems can be altered by the variation of Cl/Mg atomic ratio in catalyst based on Mg supports, whether soluble or insoluble. This effect is seen only when excess chloride is added using an aluminum-containing compound or a boron-containing compound, since both general types of compounds have similar function and behave similarly. This effect is not seen under solution polymerization conditions.

When a silicon compound such as silicon tetrachloride is used as the halogenating agent, a narrow molecular weight distribution polymer is produced even at high Cl/Mg atomic ratios. Replacing the halogenating agent with a tin halide such as tin tetrachloride results in a polymer having substantially no broadened molecular weight distribution at high Cl/Mg atomic ratios.

Magnesium siloxide compounds can be solubilized in a hydrocarbon by the addition of trialkylaluminum compounds. Trialkylaluminum compounds may be added either before or after the reaction is carried out which produces the magnesium siloxide compounds. Normally solubility is achieved by the addition of less than a mole of these trialkylaluminum compounds per mole of magnesium siloxide compounds, although at least 2 moles of trialkylaluminum will be necessary when n is much greater than 1. Support solubility is preferred in order to more closely control the particle size distribution of slurry polymerization produced resins.

Trialkylaluminum compounds useful in the practice of the present invention have the formula $Al(R^2)_3$ wherein $R^2$ denotes alkyl groups containing from 1 to 20 carbon atoms or hydrogen, at least two $R^2$ preferably being alkyl.

Representative but non-exhaustive examples of aluminum alkyls useful in the practice of the present invention are triethylaluminum, tributylaluminum, triisobutylaluminum, diethylaluminum hydride, isoprenylaluminum, and trimethylaluminum.

When utilizing the alkyl aluminum solubilizing agents, n can be equal to 0. When n is equal to 0, the magnesium compounds resemble those of U.S. Pat. No. 4,374,755. However, the materials of the present invention are contacted with a titanium tetraalkoxide, followed by halogenation, in contrast to U.S. Pat. No. 4,374,755, where titanium halides are used. The presence of the aluminum alkyl provides a soluble catalyst until halogenation, while the use of titanium alkoxide and a halogenation agent provides high activity.

When preparing magnesium compounds where n=0, siloxanes of the formula $R^3_sSi(OH)_{4-s}$ can be used, where $R^3$ is, independently, an alkyl group having from 1 to 20 carbon atoms or a cycloalkyl group, aralkyl group, aryl group or alkoxyl group having 6 to 20 carbon atoms and s is 1, 2 or 3. Siloxanes are contacted with dialkyl magnesium or alkyl magnesium alkoxy to form a hydrocarbon insoluble reaction product as defined by solubility in saturated aliphatic hydrocarbons. Specifically, solubility is defined as capable of forming a solution with a hexane at 25° C. at a concentration of at least 0.01M. This reaction product is then contacted with an aluminum alkyl of the formula $Al(R^2)_3$ to render the reaction product hydrocarbon soluble. Thereafter, the solubilized reaction product is contacted with a transition metal alkoxide as previously described, and halogenated to provide a polymerization catalyst.

Representative but non-exhaustive examples of these organic siloxanes used with aluminum alkyls are trimethylhydroxysilane, triethylhydroxysilane, triphenylhydroxysilane, diethyldihydroxysilane, dipropyldihydroxysilane, triethoxyhydroxysilane, dicyclohexyldihydroxysilane, diphenyldihydroxysilane, butyltrihydroxysilane and phenyltrihydroxysilane.

High co-catalyst to catalyst ratios are preferred to scavenge impurities. However, high ratios are detrimental in effect, in that the co-catalysts tend to over reduce the titanium and render the catalyst less active. This lowering of activity is especially true in solution polymerization operated at high reaction temperatures. Co-catalysts are also known to solubilize magnesium compounds at high temperature with the result that under solution conditions the catalyst support is eroded and dissolved by the high aluminum concentration. Therefore, in solution polymerization low co-catalyst to catalyst ratios (preferably aluminum to titanium) are often best. Therefore, under slurry polymerization conditions, the aluminum to titanium ratios should be high. In solution conditions, however, I have found that the reactions carried out at temperatures at or below about 220° C. the aluminum to titanium ratios should also be high, paralleling slurry conditions. However, for solution reactions carried out above about 220° C., the aluminum to titanium ratios should be adjusted lower in order to obtain reduced solubilization of magnesium compounds and erosion of the catalyst support.

Preferred co-catalyst to catalyst ratios are therefore from about 100 to about 2000 mole ratio of co-catalyst to catalyst respectively. These ratios range from about 100 to 2000 for slurry polymerization conditions. Under solution polymerization conditions, preferred co-catalyst to catalyst ratios range from about 10 to about 200 mole ratios respectively.

Representative but non-exhaustive examples of aluminum alkyls useful in the practice of the present invention are aluminum triethyl, aluminum tributyl, triisobutylaluminum, diethylaluminum chloride, isoprenylaluminum, trimethylaluminum, dimethylaluminum chloride, trioctylaluminum, diethylaluminum ethoxide, tridecylaluminum, trioctylaluminum, trihexylaluminum, and diethylaluminum propoxide as co-catalysts.

In preparing the catalysts of the present invention, a preferred embodiment involves reacting a polysiloxane such as polymethylhydridosiloxane at a temperature of from about 40° C. to about 90° C., with a dialkyl magnesium/aluminum alkyl solution at a silicon to magnesium to aluminum atomic ratio of about 2.1 to 1.0 to 0.1 respectively. The resultant reaction product is mixed with a tetraalkyltitanate followed by a halogenating agent such as ethylaluminum dichloride. The resultant catalyst is in a slurry form which can then be used without any washing or decantation step. The preferred magnesium to titanium atomic ratio is about 1 to about 200, preferably about 5 to 100 respectively.

The catalyst of the present invention, for use in both slurry and solution systems, is prepared so that the silicon to magnesium molar ratio is such that substantially all of the magnesium alkyl is converted to magnesium siloxides. It should be noted that an excess of some silicon compounds such as polymerhylhydridosiloxane is not detrimental except to catalyst cost and, in fact, sometimes has advantages such as in slurry powder bulk densities. The silicon to magnesium atomic ratio must be at least 2:1 but can be much higher, the excess silicon being free silicon polymers as described in the present specification, or a polymeric siloxide bound to the magnesium. In addition, catalyst efficiency in slurry polymerization is affected by the Si/Mg atomic ratio. The preferred atomic ratio for optimum catalyst efficiency is at least 2.0/1.0 (Si/Mg) to about 4.0/1.0 (Si/Mg). Lower atomic ratios are detrimental to catalyst efficiency and higher ratios show no significant improvement.

In preparing the catalysts of the present invention, one of several alternate procedures can be used. The catalyst preparation can be heated after the halogen ions are added. Temperatures of from about 50° to about 150° C. and for times ranging from about 10 minutes to several hours. The catalyst is heated for a sufficient time and this will vary widely since some halogen sources tend to react sluggishly. Heating thus improves this reaction as does increased contact time.

An alternate method of catalyst preparation requires decanting of the catalyst slurry to remove the hydrocarbon soluble halogen species. However, this method provides no advantage over the preferred method unless a large excess of the halogen source is added. Large excesses of halogen in the catalyst can increase the chlorine or halogen content of the polyethylene and cause the polyethylene to be corrosive. Yet another preparation method utility is titanium halide (preferably chloride) at sufficiently high Mg/Ti molar ratios that Ti present does not chlorinate significant portions of the MgO-Si bonds to Mg-Cl bonds and maintain the Cl/Mg ratio below 0.5. Thus if the molecular weight distribution is to be broadened, only a small amount of transition metal halides can be used as a halogen source.

In solution polymerization systems the catalyst is useful at temperatures ranging from about 120° C. to about 300° C. Under slurry polymerization conditions, the catalyst is useful under conditions known to those skilled in this art, normally about 40° C. to about 90° C. and reactor pressures of up to about 40,000 psig or greater. The use of hydrogen to control molecular weight in either system is known. These catalysts may generally be used in place of prior art catalysts without modification to the process equipment.

The catalysts of the present invention will normally be effective when residence time parameters are observed. In slurry polymerization systems the residence time should range from about 30 minutes to about 10 hours, usually from about 1 to 5 hours, while in solution polymerization systems the residence time should range from about 10 seconds to several hours, but usually from about 1 minute to about 1 hour.

These differences in residence times are due to polymerization rates and thermal deactivation of the catalyst in solution systems. Slurry polymerization temperatures give lower polymerization rates but catalysts are active for longer periods, so increased residence time can be used to obtain good catalyst utilization. Solution polymerization in contrast has high polymerization rates but catalysts will thermally deactivate such that catalyst activity decreases rapidly with time and usually becomes relatively inefficient after about one hour.

The instant invention can be carried out in either continuous or batch polymerization for commercial use, continuous polymerizations are preferred. Likewise, the reactor utilized can be a tube or a stirred tank reactor as is commonly used, but any reactor can be utilized which intimately contacts ethylene with the catalyst.

Control of molecular weight can be done utilizing hydrogen as is known in the art. In addition, molecular weight control can be provided by reactor temperature in the case of solution polymerization for a combination of hydrogen or temperature in both slurry and solution. Normally, higher temperatures will reduce molecular weight, although this effect is seen more acutely in solution polymerization systems than in slurry polymerization systems.

In slurry polymerization reactions, the catalyst is useful under conditions known to those skilled in this art, normally 40° C. to about 90° C. and total reactor pressures up to about 40,000 psig and including the use of hydrogen to control molecular weight. These catalysts may generally be used in place of prior art catalysts without modification.

The catalysts of the present invention provide narrow and broad molecular weight distributions in the obtained polymer. The molecular weight distribution in slurry polymerization systems can be altered by the variation of the Cl/Mg atomic ratio in the catalyst based on Mg supports, whether soluble or insoluble. This effect is seen only when excess chloride is added using an aluminum-containing compound or a boron-containing compound, since both general types of compounds have similar function and behave similarly. This effect is not seen under solution polymerization conditions.

For example, changing the halogen as represented by the chlorine to magnesium ratio from a 4:1 to 8:1 respectively broadens the molecular weight distribution of the polymer. It is preferred that the ratio of halogen, preferably chlorine to magnesium range from about 3:1 to about 16:1 respectively. I have found that the catalyst activity tends to decrease as the ratio of chlorine to magnesium is increased. However, I have also found that for molecular weight distribution broadening most significant mole ratios of from 6:1 to 12:1 and a mole ratio of about 8:1 halogen to magnesium is most preferred.

While the chloride to magnesium ratio affects molecular weight distribution in slurry systems, it has been surprisingly found that the molecular weight distribution is *not* affected in solution polymerization systems, but rather catalyst activity is changed. The surprising reversal of effect in solution and slurry polymerization systems is not explained, but definitely exists.

Slurry polymerization catalysts having a Cl/Mg mole ratio of 6 to 1 or more give polyethylene catalyst having a decreased catalyst efficiency. Unexpectedly, I have discovered that increasing the Si/Mg molar ratio in the catalyst improves the catalyst efficiency. A catalyst having a Cl/Mg mole ratio of 8 to 1, prepared while increasing the Si/Mg atomic ratio from 2.1 to 2.5 or higher, produced a broad molecular weight distribution polyethylene at increased catalyst efficiencies in slurry polymerization. This increase in Si/Mg atomic ratio results in about a three-fold increase in catalyst efficiency.

When carrying out a slurry polymerization the magnesium to titanium ratio should range from about 1:1 to about 50:1 respectively, while the preferred range is from about 5:1 to about 25:1 respectively. Notice should be taken that in slurry polymerization systems, as the magnesium to titanium molar ratio increases, polymer bulk density goes down while catalyst efficiency rises. It is therefore apparent to those skilled in this art that a balance between catalyst efficiency and lowered polymer bulk density must be obtained.

The invention is more concretely described with reference to the examples below wherein all parts and percentages are by weight unless otherwise specified. Examples are provided to illustrate the instant invention and not to limit it.

In the examples which follow, dibutyl magnesium was obtained as a solution in heptane from the Lithium Corporation of America. Polymethylhydridosiloxane (PMHS) was obtained from Petrarch Systems, Inc. Triethyl aluminum and ethyl aluminum dichloride were obtained as hexane solutions from Texas Alkyls, Inc. Butylethylmagnesium was obtained as a 0.640 molar solution in heptane from Texas Alkyls, Inc. The tetraisopropyltitanate was obtained from Alfa Products. Isoparaffinic mixtures were obtained from Exxon Company (ISOPAR ® E and ISOPAR ® G, trademark of and sold by Exxon Company, U.S.A.) and purified with nitrogen purging and molecular sieves to remove oxygen and water. Hexane was obtained from the Phillips Petroleum Company and purified with molecular sieves and nitrogen to remove oxygen and water. All catalyst preparations were carried out in an inert atmosphere.

EXAMPLE 1

A catalyst was prepared by reacting PMHS (3.4 milliliters, 56 millimoles silicon) to a stirred solution of 35 milliliters (ml) of 0.715 molar dibutyl magnesium and 215 ml of hexane. The solution turned cloudy in about 2 minutes. The mixture was heated to about 70° C. for 1 hour and then cooled to 25° C. The mixture was stirred and 2.0 ml of 1.0 molar tetraisopropyltitanate (2.0 millimoles) in hexane followed by 87 ml of 1.149 molar ethylaluminum dichloride (100 millimoles) was added dropwise to form a slurry.

A portion of the catalyst slurry obtained was diluted with hexane. An aliquot of this dilute catalyst containing 0.001 millimoles of titanium was added to a nitrogen purged stirred 1.8 liter reactor containing 700 ml of dry oxygen free hexane and 2.0 ml of 0.10 molar triethylaluminum. The reactor was pressured to 50 pounds per square inch gauge (psig) with hydrogen and vented to 0 psig. The procedure was repeated three times. The reactor pressure was adjusted to 30 psig with hydrogen and then 100 psig with ethylene. The reactor contents were heated to 80° C. Ethylene was added to maintain a constant reactant pressure of 150 psig. After 1 hour the reactor was cooled and vented. The reactor contents were filtered and the polyethylene recovered was dried in a vacuum oven at 40° C. until free of hexane. The recovered polyethylene weighed 103.4 grams and had a melt index as determined by ASTM 1238 condition E of 0.09. An $I_{10}/I_2$ ratio was determined wherein $I_2$ is the melt index of ASTM 1238 condition E and $I_{10}$ as a high load melt index (ASTM 1238 condition N) to give a ratio of 15.6. The higher the $I_{10}/I_2$ ratio, the broader the molecular weight distribution of the polymer. The catalyst efficiency was 2,160,000 grams of polyethylene per gram of titanium. The efficiency of this catalyst was 4,430,000 when no hydrogen was used in the polymerization.

EXAMPLE 2

Polymethylhydridosiloxane (3.4 ml, 56 mmoles silicon) was added to a stirred solution of 35.0 ml of 0.715 molar dibutyl magnesium and 215 ml of Isopar ® E and heated to about 75° C. The mixture was heated at 70° to 100° C. for ½ hour, then cooled to 30° C. After cooling, 2.5 ml of 1.0 molar tetraisopropyltitanate in hexane was added, followed by the dropwise addition of 87 ml of 1.149 molar ethyl aluminum dichloride.

The polymerization was carried out exactly as described in Example 1 using the catalyst of Example 2 except that 1.7 ml of 0.593 molar triethylaluminum and 50 psig hydrogen was used. The recovered polyethylene weighed 20 grams and had a melt index of 0.80. The $I_{10}/I_2$ ratio was 13.7 with a catalyst efficiency of 418,000 grams of polyethylene per gram titanium. Efficiency was lower because of increased hydrogen in the polymerization.

The catalyst supports used in Examples 1 and 2 were not soluble in aliphatic hydrocarbons. However, these catalysts can be solubilized in aliphatic hydrocarbons by the utilization of aluminum alkyls. Example 3 illustrates the use of aluminum alkyls to solubilize magnesium siloxide supports.

EXAMPLE 3

To a stirred solution of 112 ml. dibutylmagnesium (80.0 millimoles Mg) and 88 ml hexane was added 0.5 ml PMHS (8.2 mmoles Si). The solution was heated to about 70° C. for ½ hour and cooled to 30° C. The mixture remained a solution. Stirring was begun, followed by the addition of 0.7 ml of PMHS (11.5 mmoles Si). The solution was heated to about 70° C. for ½ hour and cooled to 35 ° C. The mixture remained a solution.

To the stirred solution was additionally added 1.2 ml of PMHS (19.7 additional millimoles Si). The solution was heated to about 70° C. for ½ hour and cooled to 35° C. The resultant solution had a Si/Mg atomic ratio of 0.49. The mixture remained a solution.

To the stirred solution was additionally added 2.5 ml PMHS (41.0 additional millimoles Si). The solution was heated to about 70° C. for ½ hour and cooled to 25° C. The resultant solution had a Si/Mg atomic ratio of 1.0 and because of the heating steps, the species in solution is believed to be $RMgOSi(R)(H)(CH_3)$, where R is a butyl group.

To the stirred solution was added an additional 4.0 ml PMHS to bring the Si/Mg atomic ratio to 2.0. The reaction exotherm heated the mixture from 25° C. to 35° C. and the mixture solidified into a clear gel. The species present in the gel formed from the reaction of PMHS and $MgR_2$ at a Si/Mg atomic ratio of 2 is believed to be magnesium disiloxide, $Mg[OSi(R)(H)(CH_3)]_2$.

To the solid gel, 13.5 ml of 0.593 molar triethyl aluminum (8.01 millimoles) was added. The gel immediately began dissolving and after mixing, a solution was obtained.

EXAMPLE 4

This example shows the effect of aluminum alkyls present during the reaction of PMHS and dialkyl magnesium. In this experiment, PMHS (25.6 ml., 420 millimoles Si) was added slowly to a stirred solution of 280 ml. of 0.715 molar dibutylmagnesium (200 millimoles Mg) and 33.7 ml. of 0.593 molar triethylaluminum (20 millimoles Al). The PMHS was added such that the exotherm of the reaction did not heat the mixture above 85° C. The stirred solution was then maintained at 70°-80° C. for one hour by heating. After cooling to room temperature, the solution was diluted with oxygen-free dry hexane to 500 ml giving a 0.40 molar magnesium disiloxide solution.

EXAMPLE 5

An experiment was carried out to show the effect of aluminum trialkyls present during the reaction of PMHS and alkyl magnesium alkoxide. In this experiment, a solution of 18.8 ml of reagent grade n-propyl alcohol (250 millimoles) in 100 ml hexane was added dropwise to a stirred solution of 391 ml of 0.640 molar butylethylmagnesium (250 millimoles). A solution of 211 ml of 0.593 molar triethylaluminum (125 millimoles) was added to the slurry. The solution was evaporated to a volume of 500 ml to give a 0.5 molar alkylmagnesium alkoxide solution. PMHS (6.4 ml., 105 millimoles Si) was added to a 200 ml aliquot of the solution. The reaction exotherm heated the solution to about 50° C. After cooling to room temperature, a solution was obtained.

EXAMPLE 6

A complete reaction sequence for preparing a solution of magnesium disiloxide where n=0.05, subsequent catalyst preparation, and polymerization of ethylene was carried out in an experiment. In this experiment, PMHS (25.6 ml. 420 millimoles Si) was added slowly to a stirred solution comprising 380 ml of 0.715 molar dibutylmagnesium (200 millimoles Mg) and 33.7 ml of 0.593 molar triethylaluminum (20 millimoles Al). The PMHS was added such that the exotherm of the reaction did not heat the mixture above 85° C. The stirred solution was then maintained at 70°-80° C. for one hour by heating. After cooling to room temperature, the solution was diluted with hexane to 500 ml, giving a 0.40 molar magnesium disiloxide solution. The catalyst was prepared by adding a solution of 2.0 ml of 1.0 molar tetraisopropyltitanate (2 millimoles) in hexane to 125 ml of the magnesium disiloxide solution (50 millimoles Mg). To this solution was added dropwise 87 ml of a 1.149 molar ethylaluminum dichloride solution (100 millimoles Al) in hexane. The resultant catalyst slurry was stirred for one hour.

The catalyst was then used in polymerization of ethylene. A portion of the catalyst slurry was diluted with hexane. An aliquot of this dilute catalyst containing 0.001 millimoles of titanium was added to a nitrogen purged, stirred, 1.8-liter reactor containing 600 ml of dry, oxygen-free hexane, and 1.7 ml of 0.593 molar triethylaluminum. The reactor was pressured to 50 psig with hydrogen and vented to 0 psig. This procedure was then repeated three more times. The reactor pressure was adjusted to 30 psig with hydrogen and then 100 psig with ethylene. The reactor contents were heated to 80° C. and then ethylene was added to maintain a constant reactor pressure of 150 psig. After one hour the reactor was cooled and vented.

The reactor contents were filtered and the polyethylene dried in a vacuum oven at 40° C. until free of hexane. The polyethylene weighed 170 grams and had a melt index (ASTM 1238, Condition E) of 1.36. The catalyst efficiency was 3,550,000 grams of polyethylene per gram of titanium. The $I_{10}/I_2$ ratio of the polymer was 9.4.

EXAMPLE 7

Procedure of Example 6 was repeated for catalyst preparation except that 5.0 ml of 1.0 molar tetraisopropyl titanate (5.0 mmole titanium) in hexane was used such that the catalyst had a magnesium to a titanium atomic ratio of 10.

Thereafter, the procedure of Example 6 using 30 psig hydrogen for ethylene polymerization was repeated using an aliquot containing 0.001 millimole of titanium of the catalyst prepared in this example. After the polymerization carried out as described in Example 6 using 30 psi hydrogen, the polyethylene obtained weighed 93.2 grams and had a melt index (ASTM 1238 condition E) of 1.08. The catalyst efficiency was 1,950,000 grams of polyethylene per gram of titanium. The $I_{10}/I_2$ ratio of the polymer was 8.5.

EXAMPLE 8

The procedure of Example 7 was repeated using 10 ml of 1.0 molar tetraisopropyl titanate (10.0 mmole titanium) in hexane in the catalyst preparation such that the resultant catalyst had a magnesium to titanium atomic ratio of 5.

Repeating the polymerization procedure of Example 7, an aliquot of the catalyst appeared therein (containing 0.001 mm of titanium) was used. The polyethylene obtained from the polymerization weighed 16.8 grams and had a melt index (ASTM 1238 Condition E) of 1.18. The catalyst efficiency was 351,000 grams of polyethylene per gram of titanium. The $I_{10}/I_2$ ratio of the polymer was 8.7. The catalyst efficiency was lower than Example 7 because the Mg/Ti atomic ratio in the catalyst was lowered from 10.0 to 5.0.

EXAMPLE 9

A siloxy magnesium chloride catalyst support is prepared and compared to a disiloxy magnesium support.

A. Catalyst Preparation

The catalyst preparation given in Example 7 was repeated except in place of the magnesium siloxide support solution a toluene support solution (125 ml; 0.4 molar in magnesium) as described in U.S. Pat. No. 3,907,759, Example 1 was used.

B. Polymerization of Ethylene

The polymerization procedure described in Example 7 was repeated using an aliquot of the catalyst described in Section A of this example containing 0.002 millimoles of titanium. The polyethylene obtained weighed 116.7 grams and had a melt index (ASTM 1238 condition E) of 0.514. The catalyst efficiency was 886,000 grams of polyethylene per gram of titanium.

EXAMPLE 10

The procedure of Example 7 was repeated except that only 15 psig hydrogen was used and 30 grams of butene-1 was added to the reactor along with the ethylene. The butene-ethylene copolymer obtained weighed 110.5 grams and had a melt index (ASTM 1238; condition E) of 0.99. The catalyst efficiency was 2,308,000 grams of polymer per gram of titanium. The polymer density as determined by ASTM D-1505, using ASTM D-1928 for the sample preparation, was 0.9317 g/cc.

EXAMPLE 11

The catalyst preparation of Example 7 was repeated using twice as much ethylaluminum dichloride so that the catalyst had a Cl/Mg atomic ratio of 8.

Repeating the polymerization procedure of Example 7 with the above catalyst and 30 psig $H_2$, 42.7 grams of polyethylene having a melt index of 0.10 was obtained. The catalyst efficiency was 891,000 grams of polyethylene per gram of titanium. The $I_{10}/I_2$ ratio of the polymer was 12.5. When the catalyst of Experiment 7 is used in a polymerization with enough hydrogen to produce a 0.10 melt index of polyethylene, the polymer would have an $I_{10}/I_2$ ratio of about 10.4.

EXAMPLE 12-16

A. Preparation of Support Solution

PMHS (25.6 ml, 420 millimoles Si) was added slowly to a stirred solution of 280 ml of 0.715 molar dibutylmagnesium (200 millimoles Mg and 33.7 ml of 0.593 molar triethylaluminum (20 millimoles Al). The PMHS was added slowly enough so that the exotherm of the reaction did not heat the mixture above 85° C. The stirred solution was then maintained at 70°-80° C. for one hour by heating. After cooling to room temperature, the solution was diluted with oxygen-free dry hexane to 500 ml giving a 0.40 molar magnesium disiloxide solution.

B. Catalyst Preparations

The volume of 1.149 molar ethylaluminum dichloride listed in Table 1 were added dropwise to stirred solutions of 125 ml of 0.4 molar magnesium solution prepared in Example 1 and 5.0 milliliters of 1.0 molar tetraisopropyltitanate in hexane. The resultant series of catalysts having different Cl/Mg molar ratios were used to polymerize ethylene.

TABLE 1

| Catalyst Example | Cl/Mg | ml 1.149 M EADC |
|---|---|---|
| 12 | 3 | 65 |
| 13 | 4 | 87 |
| 14 | 5 | 109 |
| 15 | 6 | 131 |
| 16 | 8 | 174 |

EXAMPLE 17

A portion of each catalyst slurry obtained from Examples 12-16 was diluted with hexane. An aliquot of this dilute catalyst containing 0.001 or 0.002 millimoles of titanium was added to a nitrogen-purged stirred 1.8-liter reactor containing 600 ml dry, oxygen-free hexane and 1.0 millimoles of triethylaluminum. The reactor was pressured to 50 pounds per square inch gauge (psig) with hydrogen and vented to 0 psig. The procedure was repeated three times. The reactor pressure was adjusted to 50 or 70 psig with hydrogen and then 100 psig with ethylene. The reactor contents were heated to 80° C. Ethylene was added to maintain a constant reactant pressure of 150 psig. After 1 hour, the reactor was cooled and vented. The reactor contents were filtered and the polyethylene recovered was dried in a vacuum oven at 40° C. until free of hexane. The millimoles of titanium used, hydrogen pressure, catalyst efficiency, and polymer properties are listed in Table 2.

TABLE 2

| Catalyst Number | Cl/Mg | Millimoles Titanium Used | Hydrogen psig | Catalyst Efficiency kg Pe/g Ti | $I_2$ | $I_{10}/I_2$ |
|---|---|---|---|---|---|---|
| 12 | 3 | 0.002 | 50 | 389 | 1.91 | 9.0 |
| 13 | 4 | 0.001 | 50 | 1240 | 3.80 | 8.3 |
| 14 | 5 | 0.001 | 50 | 967 | 2.29 | 9.3 |
| 15 | 6 | 0.001 | 70 | 497 | 2.78 | 9.6 |
| 16 | 8 | 0.002 | 70 | 305 | 1.92 | 10.9 |

EXAMPLE 18

Solution polymerizations were conducted to determine the effect of the Cl/Mg atomic ratio upon catalyst efficiency.

A. Catalyst Preparation

Catalysts were prepared by mixing 0.1 molar support solution, hexane, 0.1 ethylaluminum dichloride (EADC) 0.001 molar tetraisopropyltitanate (Ti(OiPr)$_4$) and 0.1 molar triethylaluminum (TEAL) solutions in hexane in the order given. The support solution was prepared as described in Example 4 and diluted with hexane. The hexane added to the catalysts was adjusted so that the final catalyst slurry had a volume of 100 ml. The exact amounts of catalyst components used are listed in Table 3.

TABLE 3

| Catalyst No. | ml., 0.1m Support Solution | ml., Hexane | ml 0.1m EADC | ml 0.001m Ti(OiPr)$_y$ | ml 0.1m TEAL | Component Atomic Ratio | | |
|---|---|---|---|---|---|---|---|---|
| | | | | | | Mg/Ti | Cl/Mg | TEAL/Ti |
| 18A | 6.3 | 62.4 | 6.3 | 12.5 | 12.5 | 50 | 2.0 | 100 |
| 18B | 6.3 | 60.9 | 7.8 | 12.5 | 12.5 | 50 | 2.5 | 100 |
| 18C | 6.3 | 59.3 | 9.4 | 12.5 | 12.5 | 50 | 3.0 | 100 |
| 18D | 6.3 | 57.8 | 10.9 | 12.5 | 12.5 | 50 | 3.5 | 100 |
| 18E | 6.3 | 56.2 | 12.5 | 12.5 | 12.5 | 50 | 4.0 | 100 |
| 18F | 6.3 | 54.6 | 14.1 | 12.5 | 12.5 | 50 | 4.5 | 100 |
| 18G | 6.3 | 53.1 | 15.6 | 12.5 | 12.5 | 50 | 5.0 | 100 |
| 18H | 6.3 | 49.9 | 18.8 | 12.5 | 12.5 | 50 | 6.0 | 100 |
| 18I | 6.3 | 40.6 | 28.1 | 12.5 | 12.5 | 50 | 9.0 | 100 |
| 18J | 6.3 | 31.2 | 37.5 | 12.5 | 12.5 | 50 | 12.0 | 100 |

B. Polymerization of ethylene

The catalysts prepared in Section A of this example were utilized in the solution polymerization of ethylene. In this polymerization, a 20 ml aliquot of the catalyst slurry containing 0.0025 millimoles of titanium was pressured with nitrogen into a stirred 1.8 liter stainless steel reactor containing 1.0 liters of ISOPAR® E, about 5 psi hydrogen, and 150 psi ethylene at a temperature of 150° C. The total reactor pressure was held constant by addition of ethylene.

After 30 minutes reaction, the reactor contents were dumped into a nitrogen purged 3.0 liter glass resin kettle equipped with a reflux condensor. The polymer solution was cooled to room temperature and the solvent removed. The weight of polymer obtained, catalyst efficiency and polymer melt index is given in Table 4.

TABLE 4

| Catalyst Number | Cl/Mg Atomic Ratio | gPE | Kg PE/g Ti | MI$_2$ |
|---|---|---|---|---|
| 18A | 2.0 | less than 1 | about 10 | — |
| 18B | 2.5 | 26.0 | 217 | .41 |
| 18C | 3.0 | 49.6 | 414 | 1.5 |
| 18D | 3.5 | 76.8 | 641 | 4.5 |
| 18E | 4.0 | 79.8 | 666 | 8.6 |
| 18F | 4.5 | 86.2 | 720 | 5.5 |
| 18G | 5.0 | 87.9 | 734 | 6.4 |
| 18H | 6.0 | 80.5 | 672 | 3.8 |
| 18I | 9.0 | 26.4 | 220 | .47 |
| 18J | 12.0 | 15.3 | 128 | .42 |

Molecular weight distribution as measured by $I_{10}/I_2$ ratios showed no significant broadening in these solution polymerizations.

This data indicates that the polymer molecular weight distribution for solution polymerizations is independent of Cl/Mg atomic ratio and the optimum Cl/Mg atomic ratio for highest catalyst efficiency is about 4 to 6 (based on magnesium of 1.0).

EXAMPLE 19

The effect of higher Si/Mg atomic ratios on catalyst efficiency is illustrated

A. Catalyst Preparation

The catalyst preparation of Example 16 was repeated using sufficient polymethylhydridosiloxane to provide a Si/Mg atomic ratio of 2.5.

B. Catalyst Preparation

The catalyst preparation of Example 16 was repeated using sufficient polymethylhydridosiloxane to provide a Si/Mg atomic ratio of 3.0.

C. Polymerization of Ethylene

The polymerization procedure of Example 17 was repeated using catalysts of Sections A and B of this example and 70 psi hydrogen. The amounts of titanium used and the results obtained are listed in Table 5. $I_2$ was determined as described in Example 4.

TABLE 5

| Catalyst | Si/Mg Atomic Ratio | Milimoles Titanium Used | Catalyst Efficiency | I$_2$ |
|---|---|---|---|---|
| Example 16 | 2.1 | .002 | 305 | 1.92 |
| Example 19A | 2.5 | .004 | 628 | 3.55 |
| Example 19B | 3.0 | .001 | 1330 | 3.76 |

EXAMPLE 20

A. Catalyst Preparation

The catalyst preparation of Example 7 was repeated except that 5.0 ml of 1.0 molar titanium tetrachloride (5.0 millimoles titanium) was substituted for tetraisopropyltitanate.

B. Polymerization of Ethylene

The polymerization procedure of Example 17 was repeated using an aliquot containing 0.001 millimoles of titanium as the catalyst prepared in section A of this Example, 50 psig hydrogen, and 0.125 millimoles of triethylaluminum. The polyethylene obtained weighed 74.8 grams, had a melt index of 3.08 and an $I_{10}/I_2$ ratio of 8.3. The catalyst efficiency was 1,560,000 grams of polyethylene per gram of titanium.

EXAMPLE 21

A. Catalyst Preparation

The catalyst preparation of Example 11 was repeated substituting 5.0 ml 1.0 molar titanium tetrachloride (5.0 millimoles titanium) for tetraisopropyltitanate.

B. Polymerization of Ethylene

The polymerization procedure of Example 21 was repeated using 0.25 millimoles of triethylaluminum and an aliquot of the catalyst prepared in Section A of this example, which contained 0.002 millimoles of titanium. The polyethylene obtained weighed 70.4 grams, had a melt index of 1.16 and an $I_{10}/I_2$ ratio of 10.1. The catalyst efficiency was 735,000 grams of polyethylene per gram of titanium.

A comparison of Example 20 and 21 illustrates that a halide containing titanium can be used and the polymer molecular weight distribution varied from narrow to broad by the Cl/Mg atomic ratio, when the chloride is provided by ethylaluminum dichloride.

EXAMPLE 22

A. Support Solution Preparation

Polymethylhydridosiloxane (1502 millimoles Si, 91.6 ml) was added slowly to 1000 ml of 0.715 molar dibutylmagnesium (715 millimoles Mg) and 79.6 ml of 0.898 molar triethylaluminum (71.5 millimoles Al). The exothermic reaction was controlled to under about 80° C. and then maintained by heating at 70° C. for 1 hour. The solution was cooled to room temperature. Analysis for magnesium determined the solution to be 0.632 molar in magnesium.

B. Catalyst Preparation

A solution of silicon tetrachloride (11.5 ml; 100 millimoles Si) in 100 ml of hexane was added dropwise over a period of about 1 hour to a solution of 79.0 ml of the support solution from Section A of this example (50 millimoles Mg), 46 ml hexane, and 4.72 ml of 1.060 molar tetraisopropyltitanate (5.0 millimoles Ti). A solution was formed but solids formed overnight.

C. Polymerization of Ethylene

The catalyst of Section B (this experiment) was allowed to age for two weeks. A portion of the catalyst containing 0.008 millimoles of titanium was added to a 1.8 liter stirred stainless steel reactor containing 1.0 millimoles of triethylaluminum and 600 ml of hexane. The reactor was pressured to 50 psig with and vented to 0 psig. This procedure was repeated a total of three times. The hydrogen pressure was then adjusted to 50 psig and ethylene added to give a total pressure of 100 psig. The reactor contents was heated to 80° C. and the total reactor pressure adjusted to 150 psig. The polymerization was conducted for 1.0 hour with the total reactor pressure maintained at 150 psig by addition of ethylene. After 1.0 hour the reactor was cooled, the reactor contents collected and the polymer collected by filtration. After drying in a vacuum at 60° C. until free of hexane, 6.7 grams of polyethylene was obtained. The polymer had a melt index of 0.71 and an $I_{10}/I_2$ ratio of 7.2. The catalyst efficiency was 17,000 grams of polyethylene per gram of titanium.

This example illustrates that silicon tetrachloride is not effective in producing high efficiency catalysts using the support solution of this invention along with a tetraalkoxytitanium as the titanium source. Also, the polymer had a narrow molecular weight distribution even though the Cl/Mg atomic ratio was 8.0.

EXAMPLE 23

A. Catalyst Preparation

The catalyst preparation of Example 22, section B was repeated replacing the silicon tetrachloride with 11.7 ml of tin tetrachloride (100 millimoles Sn). A catalyst slurry formed immediately.

B. Polymerization of Ethylene

The polymerization procedure of Example 22, section C was repeated using 0.25 millimoles of triethylaluminum and an aliquot of catalyst slurry from Section A of this example containing 0.002 millimoles of titanium. The polymer obtained weighed 91.9 grams, had a melt index of 4.01, and an $I_{10}/I_2$ ratio of 7.0. The catalyst efficiency was 959,000 grams of polyethylene per gram of titanium. This example illustrates the use of tin tetrachloride as a halogenating agent to prepare a high efficiency catalyst according to this invention. However, the molecular weight distribution is very narrow.

Molecular weight distribution was determined using the ratio $I_{10}/I_2$, where the result indicates the relative molecular weight distributions, as described by Nielsen in *Polymer Rheology* pp 69–75, Marcel Dekker pub, N.Y. (1977). In this determination, $I_2$ is the melt index as determined by ASTM 1238, condition E, and $I_{10}$ is the melt index as determined by ASTM 1238, condition N.

Thus it is apparent that the catalysts of the present invention provide extremely high efficiency, ease of preparation, require no purification or washing techniques, and allow the control of molecular weight distribution in the resultant polymer.

While certain embodiments and details have been shown for the purpose of illustrating this invention, it will be apparent to those skilled in this art that various changes and modifications may be made herein without departing from the spirit or scope of the invention.

I claim:

1. An olefin polymerization catalyst comprising a magnesium-containing support of the general formula

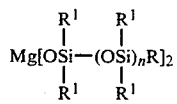

reacted with non-halide transition metal compounds and halide compounds, wherein the transition metal compounds are selected from the group consisting of titanium, vanadium, chromium and zirconium alkoxides and the halide compounds are hydrocarbon soluble and wherein such halides are aluminum halides, boron halides or mixtures of these, the SiOMg/Mg ratio is at least 1.0, and the halogen/Mg ratio is at least 2.0, wherein each $R^1$ is, independently, hydrogen, alkyl groups containing from 1 to 20 carbon atoms, aryl groups, aralkyl groups, or alkaryl groups containing from 6 to 20 carbon atoms, and n is greater than 0.

2. An olefin polymerization catalyst comprising a polymeric magnesium-containing support of the general formula

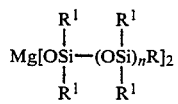

reacted with transition metal compounds and halide compounds, wherein the transition metal compounds are selected from the group consisting of titanium, vanadium, chromium and zirconium alkoxides and halides and the halide compounds are hydrocarbon soluble and wherein at least 80 mole percent halides present are provided by aluminum halides, boron halides, or mixtures of these, the SiOMg/Mg ratio is at least 1.0, and the halogen/Mg ratio is at least 2.0, wherein each $R^1$ is, independently, hydrogen, alkyl groups containing from 1 to 20 carbon atoms, aryl groups, aralkyl groups, or alkaryl groups containing from 6 to 20 carbon atoms, aryl groups, aralkyl groups, or alkaryl groups containing from 6 to 20 carbon atoms, and n is greater than 1.

3. A catalyst as described in claim 2 wherein the halogen is chlorine.

4. A catalyst as described in claim 3 wherein n is from about 1 to about 50.

5. A method for the preparation of an olefin polymerization catalyst comprising combining (1) the reaction product of a hydropolysiloxane of the general formula

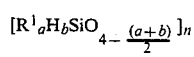

wherein R¹ is selected from the group consisting of hydrogen, halogen, alkyl groups containing from 1 to 20 carbon atoms, aryl groups, aralkyl groups, alkaryl groups and acyloxy groups, each containing from 6 to 20 carbon atoms, a is from 0.1 to 2, b is greater than 0 and n is greater than 0, where the sum of a and b does not exceed 3, with a dialkyl magnesium or alkyl magnesium alkoxide of the general formula RMgR or RMgOR wherein each R is, independently, hydrogen, alkyl groups containing from 1 to 20 carbon atoms, aryl groups, aralkyl groups and alkaryl groups each containing from 6 to 20 carbon atoms, to form a reaction product having a SiO/Mg molar ratio of at least 1.0, with (2) non-halide transition metal alkoxides having at least one of the general formulas RO[M(OR)$_2$O]$_p$R or MO$_q$(OR)$_r$ or R$_x$M(OR)$_y$ where M is titanium, vanadium, chromium or zirconium and R is an alkyl group containing from 1 to 20 carbon atoms, aryl groups, aralkyl groups and alkoxyl groups each containing from 6 to 20 carbon atoms, q is 0 or 1, r is from 2 to 4, and 2q+r is equal to the valence of M; p is at least 2; and x+y is equal to the valence of M, and (3) a halogenating agent to obtain a polymerization catalyst having a halogen to magnesium ratio of at least 2.0.

6. A method as described in claim 5 wherein the reaction product of (1) is contacted with (2) followed by reaction with (3).

7. A method as described in claim 6 wherein the reaction product of (1) is contacted with (3) followed by reaction with (2).

8. A method as described in claim 6 wherein a is from 0.1 to 2 and b is 1, 2 or 3.

9. A method as described in claim 8 wherein the hydropolysiloxane contains at least one material selected from the group consisting of polymethylhydrosiloxane (PMHS), polyethylhydrosiloxane, polymethylhydro-dimethylsiloxane copolymer, polymethylhydro-methyloctylsiloxane copolymer, polyethoxy hydrosiloxane, tetramethyldisiloxane, diphenyldisiloxane, trimethylcyclotrisiloxane, tetramethylcyclotetrasiloxane, polyphenylhydrosiloxane, polychlorophenylhydrosiloxane.

10. A method as described in claim 9 wherein the dialkyl magnesium contains at least one material selected from the group consisting of dibutylmagnesium, n-butyl-secbutyl magnesium, butylethylmagnesium, butyloctylmagnesium di-n-hexylmagnesium.0.02 trimethylaluminum, di-n-butylmagnesium. 2 triethylaluminum, di-n-butylmagnesium,.0.1 triethylaluminum, dibutylmagnesium.½ triisobutylaluminum, dibutylmagnesium.2 triisobutylaluminum, butyloctylmagnesium 2 triisobutylaluminum, butyloctylmagnesium.½ triethyl aluminum, butylethylmagnesium 0.01 triethylaluminum, and mixtures of these.

11. A method as described in claim 10 wherein the transition metal alkoxide contains at least one material selected from the group consisting of tetraisopropyltitanate, tetra-n-butyltitanate, tetrabis(2-ethylhexyl)-titanatum, tri-n-butyl vanadate, tetra-n-propylzirconate and tetra-n-butylzirconate, iso-C$_3$H$_7$-O [Ti(O-iso-C$_3$H$_7$)$_2$-O]$_{10}$ isoC$_3$H$_7$, butyl (triisopropoxy) titanium and mixtures thereof.

12. A method as described in claim 11 wherein the halogenating agent is a chlorinating agent.

13. A method as described in claim 12 wherein the chlorinating agent is at least one material selected from the group consisting of alkylaluminum dichloride, dialkylaluminum chloride, and alkylaluminum sesquichloride, wherein the alkyl is, independently, methyl, ethyl or isobutyl.

14. A method as described in claim 5 when carried out in the presence of aluminum alkyls added prior to (3).

15. A method as described in claim 14 wherein step (1) comprises reacting in addition to the hydropolysiloxane a hydroxysilane of the formula R$_s$Si(OH)$_{4-s}$), then contacting with aluminum alkyls, wherein s is from 1 to 3 and R is as described.

16. A method as described in claim 15 wherein R is C$_1$ to C$_{20}$ alkyl, s is from 1 to 3, (1) is carried out using RMgR . (AlR$^2$ $_3$)$_n$ and n is greater than 0.

17. A method as described in claim 16 wherein n is from about 0.1 to about 10.0.

18. A method as described in claim 17 wherein the hydropolysiloxane contains at least one material selected from the group consisting of polymethylhydrosiloxane (PMHS), polyethylhydrosiloxane, polymethylhydro-dimethylsiloxane copolymer, polymethylhydro-methyloctylsiloxane copolymer, polyethoxy hydrosiloxane, tetramethyldisiloxane, diphenyldisiloxane, trimethylcyclotrisiloxane, tetramethylcyclotetrasiloxane, polyphenylhydrosiloxane, polyeicosylhydrosiloxane, polyethylchlorohydrisiloxane, and mixtures of these.

19. A method as described in claim 18 wherein the dialkyl magnesium contains at least one material selected from the group consisting of dibutylmagnesium, n-butyl-secbutyl magnesium, butylethylmagnesium, butyloctylmagnesium, di-n-hexylmagnesium complexes 0.02 triethylaluminum, di-n-butylmagnesium . 0.1 triethylaluminum, dibutylmagnesium . ½ triisobutylaluminum, dibutyl magnesium . 2 triisobutylaluminum, butyloctylmagnesium . ½ triethylaluminum, butylethylmagnesium . 0.1 triethylaluminum, and mixtures.

20. A method as described in claim 19 wherein the transition metal alkoxide contains at least one material selected from the group consisting of tetraisopropyltitanate, tetra-n-butyltitanate, tetra(2-ethylhexyl)titanate, iso-C$_3$H$_7$-O[Ti(O-iso-C$_3$H$_7$)$_2$-]$_{10}$ iso-C$_3$H$_7$, butyl (triisopropoxy) titanium and mixtures thereof.

21. A method as described in claim 20 wherein the halogenating agent is a chlorinating agent.

22. A method as described in claim 21 wherein the chlorinating agent is selected from the group consisting of ethylaluminum dichloride, diethylaluminum, chloride, ethylaluminum sesquichloride, isobutyl and methyl analogues, SnCl$_4$, SiCl$_4$, HCl, HSiCl$_3$, aluminum chloride, ethylboron dichloride, boron chloride, diethylboron chloride, HCCl$_3$, PCl$_3$, POCl$_3$, acetyl chlorides, thionyl chloride, sulfur chloride, methyl trichlorosilane, dimethyl dichlorosilane, TiCl$_4$, and VCl$_4$.

23. A method as described in claim 22 wherein the chlorinating agent is selected from the group consisting of ethylaluminum dichloride, diethylaluminum chloride, ethylaluminum sesquichloride, and isobutyl and methyl analogues of these.

24. A method for preparing an olefin polymerization catalyst comprising
   (1) reacting a silane of the formula $R^3{}_sSi(OH)_{4-s}$ with a dialkyl magnesium or alkylmagnesium alkoxide of the formula RMgR or RMgOR to form a hydrocarbon insoluble reaction product having a Si-OMg/Mg ratio of at least 1.0, then
   (2) contacting the product of (1) with an aluminum alkyl of the formula $Al(R^2)_3$ to render the product hydrocarbon soluble, and
   (3) contacting (2) with a transition metal alkoxide having at least one general formula $RO[M(OR)_2O]_pR$; $MOg(OR)_r$; or $R_rM(OR)_y$ (4) reacting the mixture of (2) and (3) with a halogenating agent to obtain a polymerization catalyst having a halogen to magnesium ratio of at least 2, wherein each R and $R^2$ is, independently, alkyl groups, aralkyl groups and alkaryl groups containing from 6 to 20 carbon atoms, each $R^3$ is hydrogen or alkyl groups containing from 1 to 20 carbon atoms, s is from 1 to 3, g is 0 or 1, r is 2 to 4, p is at least 2, x+y equals the valence of M, and 2qr is equal to the valence of M.

25. A method as described in claim 24 wherein the halogen is chlorine and the chlorine to magnesium ratio of the catalyst is from about 3 to 1 to about 16 to 1.

26. A method as described in claim 25 wherein the halogen is chlorine and the chlorine to magnesium ratio of the catalyst is from about 3 to 1 to about 16 to 1.

27. A method as described in claim 26 wherein the halogen is chlorine and the chlorine to magnesium ratio of the catalyst is from about 3 to 1 to about 16 to 1.

28. Supported transition metal olefin polymerization catalysts for broadening molecular weight distribution in produced polymers from slurry polymerizations, wherein the transition metal catalyst support contains magnesium and silicon as a magnesium siloxide which is reacted with at least one transition metal compound and a halide compound to form a catalyst, comprising providing excess halide to the catalyst such that the total halide to total magnesium atomic ratio is at least 2.0, and the total silicon to total magnesium atomic ratio is at least 2.0, wherein said excess halide is provided from a compound of aluminum, boron, or mixtures of these, and wherein the excess halide amounts to at least 80 mole percent of the total halide content of the catalyst.

29. Catalysts as described in claim 28 wherein the excess chlorine is obtained from an aluminum compound and the Cl/Mg ratio is from about 4 to about 8.

30. Catalysts as described in claim 29 wherein the aluminum compound is selected from the group consisting of alkyl aluminum dichloride, dialkyl aluminum chloride, alkyl aluminum sesquihalide, where the alkyl is methyl, ethyl, isobutyl or mixtures thereof.

* * * * *

UNITED STATES PATENT AND TRADEMARK OFFICE
CERTIFICATE OF CORRECTION

PATENT NO. : 4,511,669
DATED : April 16, 1985
INVENTOR(S) : Donald E. Gessell

It is certified that error appears in the above-identified patent and that said Letters Patent are hereby corrected as shown below:

Column 5, line 54, "of" should be --or--.

Column 5, line 54, "90 mole percent" should be --(90 mole percent or more).--

Signed and Sealed this

Twenty-seventh Day of August 1985

[SEAL]

Attest:

DONALD J. QUIGG

Attesting Officer    Acting Commissioner of Patents and Trademarks